(12) United States Patent
Smith et al.

(10) Patent No.: US 6,825,838 B2
(45) Date of Patent: Nov. 30, 2004

(54) 3D MODELING SYSTEM

(75) Inventors: Matthew Warren Smith, Tulsa, OK (US); Kevin Michael Kelly, Venice, CA (US); Roger Royce, Venice, CA (US)

(73) Assignee: Sonocine, Inc., Venice, CA (US)

( * ) Notice: Subject to any disclaimer, the term of this patent is extended or adjusted under 35 U.S.C. 154(b) by 77 days.

(21) Appl. No.: 10/270,177

(22) Filed: Oct. 11, 2002

(65) Prior Publication Data

US 2004/0070582 A1 Apr. 15, 2004

(51) Int. Cl.[7] .............................................. G06T 15/00
(52) U.S. Cl. ...................... 345/419; 345/420; 345/582; 345/619
(58) Field of Search ................................ 345/419, 420, 345/423, 424, 427, 582, 583, 589, 620, 426, 619, 442, 441, 421, 463; 600/463

(56) References Cited

U.S. PATENT DOCUMENTS

| | | | |
|---|---|---|---|
| 4,094,306 A | 6/1978 | Kossoff | 128/2 V |
| 4,167,180 A | 9/1979 | Kossoff | 128/660 |
| 4,347,850 A | 9/1982 | Kelly-Fry et al. | 128/660 |
| 4,489,729 A | 12/1984 | Sorenson et al. | 128/660 |
| 4,905,700 A | 3/1990 | Wokalek et al. | 128/660.01 |
| 5,152,290 A | 10/1992 | Freeland | 128/660.07 |
| 5,318,028 A | 6/1994 | Mitchell et al. | 128/660.08 |
| 5,329,929 A | 7/1994 | Sato et al. | 128/660 |
| 5,333,612 A | 8/1994 | Wild | 128/660.9 |
| 5,433,202 A | 7/1995 | Mitchell et al. | 128/660.08 |
| 5,454,371 A | 10/1995 | Fenster et al. | 128/660.07 |
| 5,474,072 A | 12/1995 | Shmulewitz | 128/660.09 |
| 5,479,927 A | 1/1996 | Shmulewitz | 128/660.09 |
| 5,487,387 A | 1/1996 | Trahey et al. | 128/660.02 |
| 5,524,636 A | 6/1996 | Sarvazyan et al. | 128/774 |
| 5,562,095 A | 10/1996 | Downey et al. | 128/660.09 |
| 5,640,956 A | 6/1997 | Getzinger et al. | 128/653.1 |
| 5,664,573 A | 9/1997 | Shmulewitz | 128/660.09 |
| 5,833,634 A | 11/1998 | Laird et al. | 600/587 |
| 5,842,473 A | 12/1998 | Fenster et al. | 128/660.09 |
| 5,860,934 A | 1/1999 | Sarvazyan | 600/587 |
| 5,938,613 A | 8/1999 | Shmulewitz | 600/461 |
| 5,984,870 A | 11/1999 | Giger et al. | 600/443 |
| 5,989,199 A | 11/1999 | Cundari et al. | 600/587 |
| 6,002,958 A | 12/1999 | Godik | 600/407 |
| 6,117,080 A | 9/2000 | Schwartz | 600/443 |
| 6,119,033 A | 9/2000 | Spigelman et al. | 427/429 |
| 6,262,740 B1 | 7/2001 | Lauer et al. | 345/424 |
| 6,343,936 B1 * | 2/2002 | Kaufman et al. | 434/262 |

FOREIGN PATENT DOCUMENTS

| | | |
|---|---|---|
| EP | 0452532 A1 | 10/1991 |
| WO | 00/51484 | 9/2000 |

* cited by examiner

Primary Examiner—Kimbinh T. Nguyen
(74) Attorney, Agent, or Firm—Fulbright & Jaworski L.L.P.

(57) ABSTRACT

A computer-based 3D modeling system for constructing a virtual 3D representation from a plurality of data images of 2D cross sections having a mutual spatial relationship. The plurality of data images and the associated orientation and positioning information are extractable from a data source module. A frame creation module constructs a rectangular frame for each image slice. A texture-mapping module maps the image slice onto the associated frame as a texture. A rotation transform module rotates each frame appropriately about one or more axes based upon the orientation information associated with each data image to achieve the correct orientation in 3D space. A translation transform module translates each frame based upon the positioning information associated with each data image to achieve the correct position in 3D space.

43 Claims, 3 Drawing Sheets

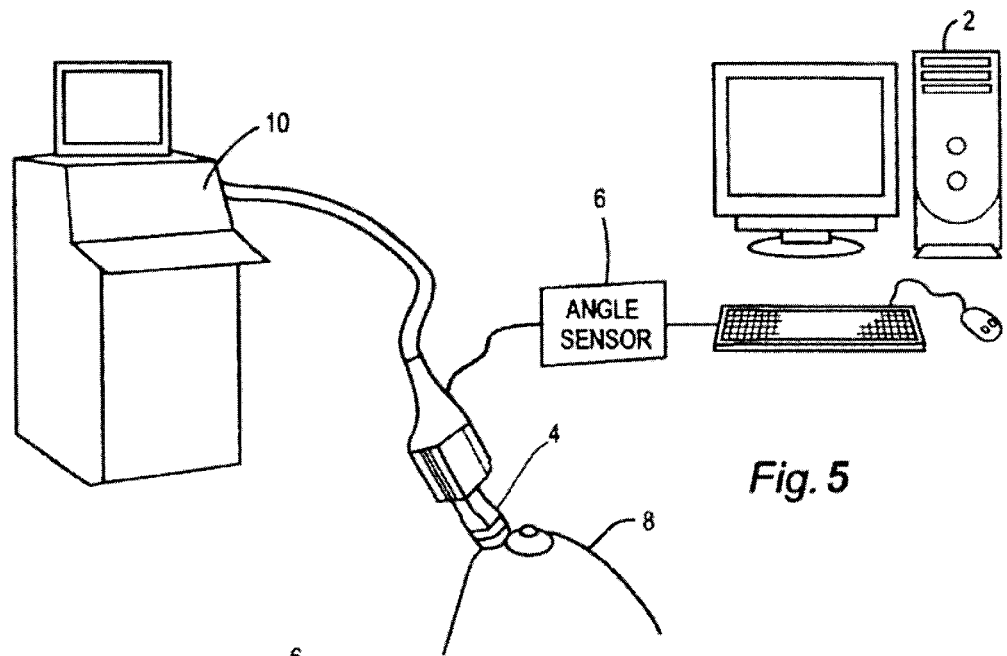
*Fig. 5*
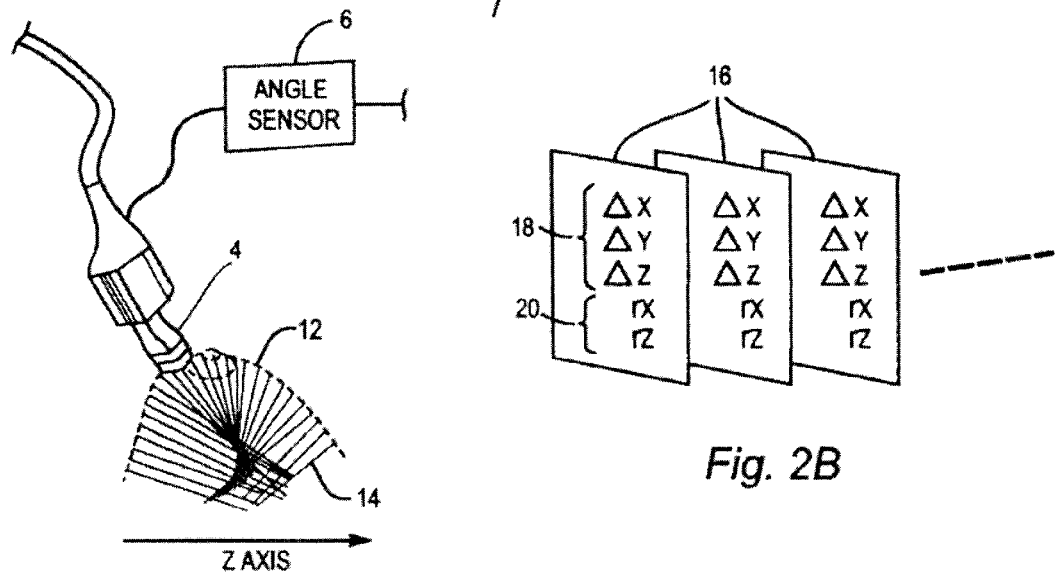
*Fig. 2A*
*Fig. 2B*
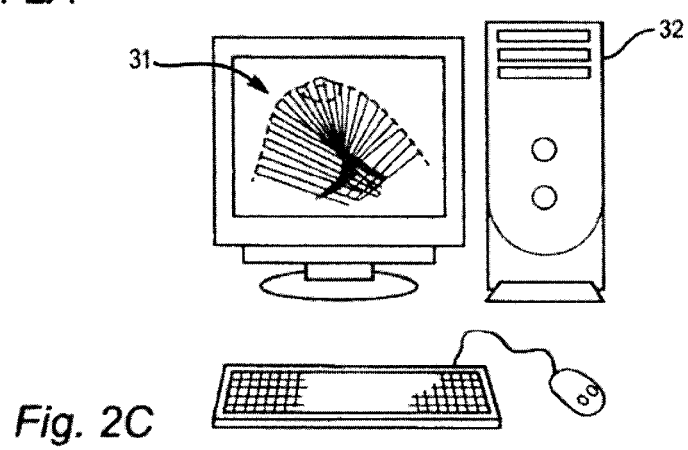
*Fig. 2C*

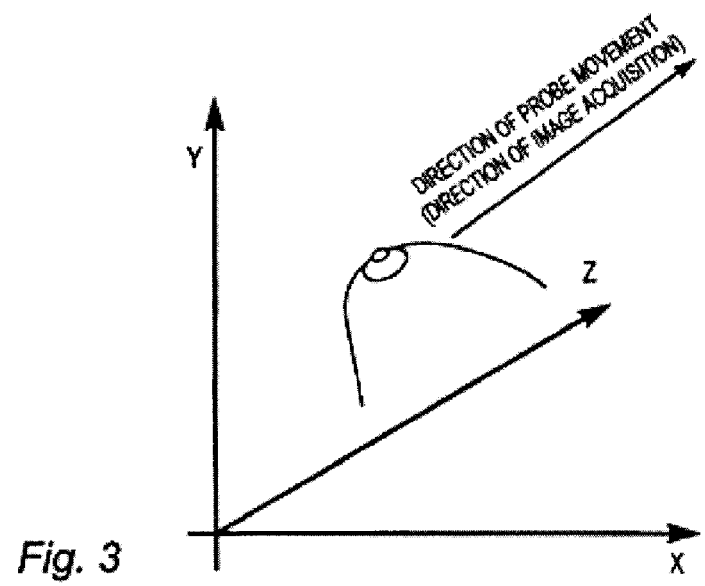
*Fig. 3*
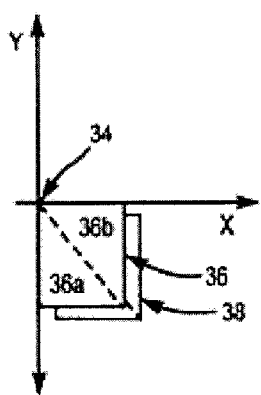
*Fig. 4A*
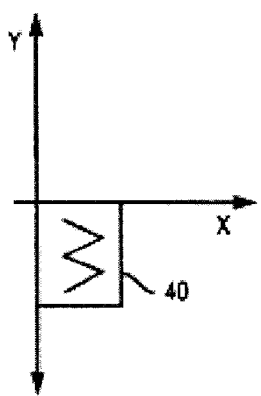
*Fig. 4B*
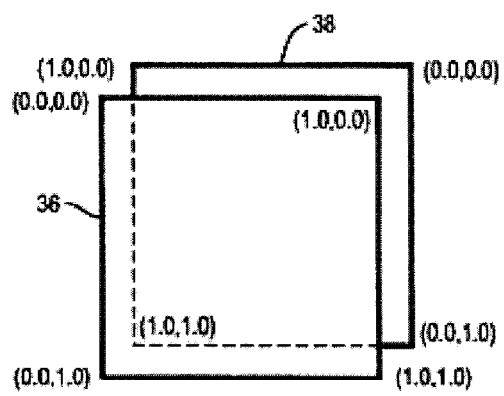
*Fig. 6*
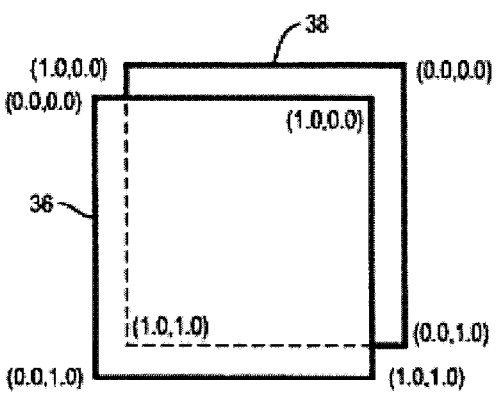
*Fig. 4C*
*Fig. 4D*

3D MODELING SYSTEM

BACKGROUND OF THE INVENTION

1. Field of Invention

The field of the present invention is 3D modeling on a computer system. More specifically, the present invention concerns itself with a way to construct a 3D computer representation of a solid object given a number of 2D image "slices" of the object.

2. Background of the Invention

There are many specialized techniques for creating image slices of real-world three-dimensional objects. In the medical imaging realm, for example, scanning devices relying on ultrasound, x-ray, and magnetic resonance technologies can be used to capture a series of image slices of various body structures as the scanning probe is moved slowly over the structure. However, assembling a 3D computer model of the structure from those 2D slices can be somewhat problematic.

The usual technique in prior art for constructing a 3D model of a solid object from a set of 2D image slices is to iteratively map each picture element (or pixel) (x,y) in each 2D image to a volume element (or voxel) (x',y',z') in 3D space; given knowledge of the orientation of each 2D image slice relative to some fixed reference point (or the other image slices used to construct the 3D model), converting 2D pixels to 3D voxels is a relatively straight-forward mathematical exercise. However, it is a relatively expensive operation, computationally, and, hence, tends to be a very slow operation when done in software. (Commercial video acceleration boards for personal computers that do this sort of mapping in hardware are not commonly available.) Also, because voxels are typically represented using multiple floating-point values, building a 3D model this way on any computer system smaller than a high-end graphics workstation places a prohibitive load on system resources when constructing a model of any useful complexity.

Therefore, it would be useful to be able to construct a solid 3D model from a set of 2D image slices without mapping individual 2D image slice pixels directly to 3D voxels. Moreover, it would be desirable to be able to do this model creation in a way that takes advantage of widely available acceleration hardware circuitry.

Typical 3D display units that are based on voxels, particularly in the field of medical imaging, are limited in their ability to quickly manipulate the rotation, viewpoints, and appearance of 3D models in order to assist the user in identifying and/or diagnosing particular structures or anomalies. It is desirable to be able to perform such manipulations, particularly on commonly-available computing hardware.

SUMMARY OF THE INVENTION

The present invention is directed towards a computer-based 3D modeling system for constructing a virtual 3D representation from a plurality of data images of 2D cross sections having a mutual spatial relationship. The virtual 3D representation is constructed by extracting from a data source module the plurality of data images and the associated orientation and positioning information, creating a planar frame for each of the data images using a frame creation module, mapping each data image onto its corresponding frame as a texture using a texture-mapping module, rotating each planar frame according to the orientation information using a rotation transform module, and translating each planar frame according to the positioning information using a translation transform module.

Once the virtual 3D representation has been constructed, it may be rendered for purposes of review and/or manipulation. Review of the virtual 3D representation may be achieved by displaying it on a screen and performing one or more manipulations including rotating the representation, advancing into the representation using a clipping plane, adjusting the translucency, transparency, color, contrast, or brightness of the representation, resizing the representation, dynamically translating the viewpoint into the representation, or dynamically moving the viewpoint relative to the representation.

BRIEF DESCRIPTION OF THE DRAWINGS

In the drawings, wherein like reference numerals refer to similar components:

FIG. 2A depicts a probe with an attached angle sensor being passed over an object, capturing a series of image slices of that object;

FIG. 2B depicts a series of image slices arranged in the order they were obtained, along with associated orientation and position information;

FIG. 2C depicts a series of image slices arranged at the angles at which they were originally obtained;

FIG. 3 depicts the direction of image slice acquisition (along the z-axis) in physical space when an object is scanned for 3D computer modeling;

FIG. 4A depicts front and back rectangular planar image frames;

FIG. 4B depicts an image that is texture mapped onto a planar frame;

FIG. 4C depicts a graphic planar frame that is rotated to an orientation in 3D space;

FIG. 4D depicts a graphic planar frame that is translated to a position in 3D space;

FIG. 5 depicts a probe attached to an ultrasound scanning device and an angle sensor, and the ultrasound scanning device and the angle sensor are connected with a personal computer system; and FIG. 6 depicts typical frame vertex coordinates for both the "front side" and "back side" of a planar frame.

DETAILED DESCRIPTION OF THE PREFERRED EMBODIMENT

Figure 1:
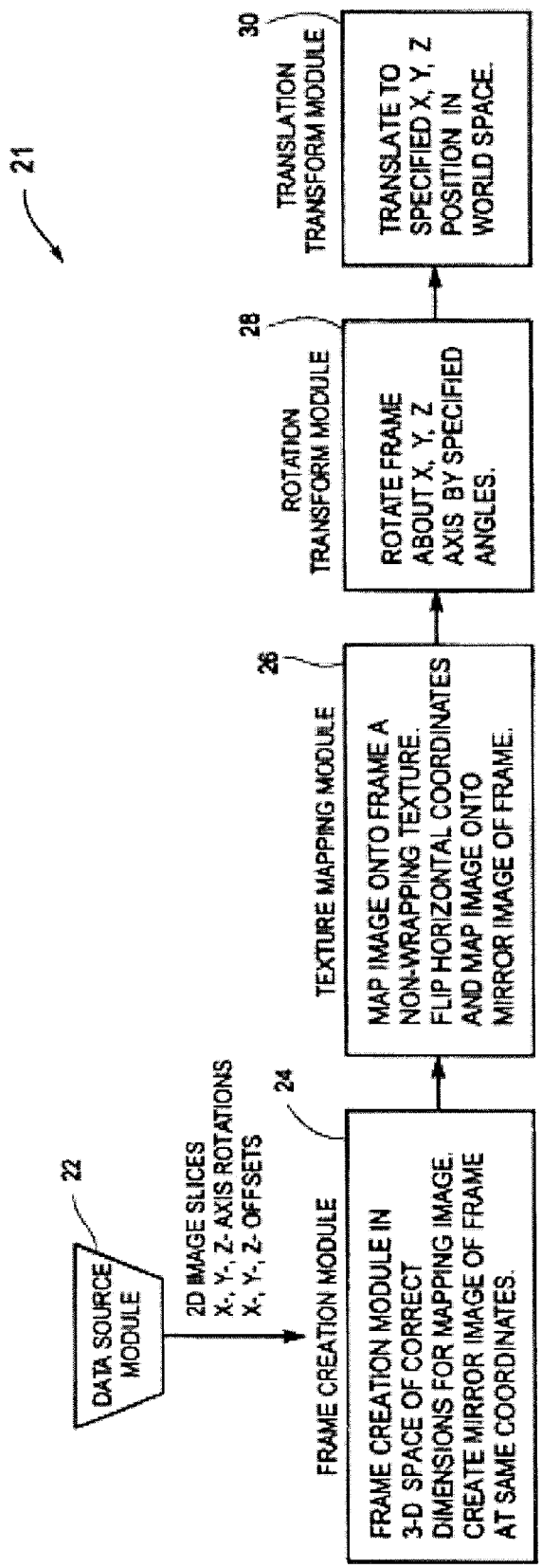
FIG. 1 is a block diagram of the 3D Modeling System, showing each of its component modules.

As shown in FIG. 1, the computer-based 3D modeling system 21 is comprised of software that is composed of several modules. The modules are used in combination to create a virtual 3D representation from a plurality of data images of 2D cross sections and the mutual spatial relationship data associated with each data image. As shown in FIG. 5, a preferred embodiment of the 3D modeling system 21 may be a subsystem of a medical imaging device, although the 3D modeling system 21 disclosed herein could be used with virtually any type of digital images that represent a series of cross sections of any substance or structure. A probe 4 connected to a rotation angle sensor 6 may be slowly and uniformly moved over the cellular tissue being scanned 8, and sequential image slices may be captured by a standard medical ultrasound scanning device 10. The scanner and the angle sensor may be attached to a personal computer 2 so that the software can acquire both the image slices and their orientation angles in 3D space. The typical format of the image slices on the computer is bitmap, but other formats could be used. Because the movement of probe 4 may be achieved by mechanical means (not shown), and its rate and direction of motion known, the offset of each of the images in 3D space may be easily determined by well known position determining devices. Such a position determining device may also be connected to the personal computer 2 for simultaneous acquisition of the position of each image.

Certain embodiments of an ultrasound scanner that could provide image slices, orientation angles and position information to a computer are disclosed in U.S. patent application Ser. No. 09/687,128, and PCT Application No. PCT/US 01/32392, the disclosures of which are incorporated herein by reference. Any set of digital images that represent a series of cross-sectional slices of any object (not just cellular tissue 8) could be modeled and used in the manner described herein. Such images could include, but are not limited to, x-rays, magnetic resonance imaging, computerized axial tomography, ultrasound, positron emission tomography, radionuclide imaging, etc. Such images could even include things like geologic cross sections from seismic or other systems, so long as sufficient images are available to construct the model.

The manner in which the images are obtained is not critical to the 3D modeling system 21 disclosed herein. To ease discussion of how such images are acquired and subsequently used by the 3D modeling system 21, however, this application will generally discuss the ultrasound embodiments disclosed in the aforementioned applications.

For discussion purposes, the spatial axes may be arbitrarily labeled. Assuming the object to be scanned is a patient's tissue, and the subject patient is lying supine for scanning, the x-axis extends from shoulder-to-shoulder (the positive x direction pointing outward from the patient's right shoulder), the y-axis is perpendicular to the patient's body (the positive y direction pointing upward from the patient's chest), and the z-axis extends from head-to-foot (the positive z direction pointing outward from the soles of the patient's feet). In a preferred embodiment successive scanned images may be acquired by moving the scanning probe in the positive z direction, as shown in FIG. 3, but movement of the probe in any direction over the subject being imaged could yield images that could be modeled.

As shown in FIG. 2A, a probe 4 may be free to tilt in two directions (about the x- and z-axes) to follow the contour of a patient's tissue 12 (such as the skin of a breast) while remaining perpendicular to the tissue or skin 12. The rotation angles of the probe about the x and z axes may be tracked by the angle sensor 6, which may then be correlated with the images so that every image has its orientation (rotation angle) information. The speed of the probe's traversal motor (not shown) may be controlled via feedback from the angle sensor 6 such that the motor moves the probe along the z-axis at a variable rate in such a manner that keeps the probe's velocity over the skin 12 constant despite changes in the skin's contour angle. Thus, because the rate of image capture may be fixed by the scanning hardware and remain constant, in such an embodiment the top edges of the captured image slices 14 are equidistant from one another and parallel to one another with respect to the z axis.

Importantly, however, nothing about the present invention requires that any edge of the acquired image slices 14 be equidistant or parallel to one another along any axis. So long as sufficient orientation (rotation angle) information is gathered for each image, along with information about the position of each image, the images could be modeled and used as described herein. For example, the rotation angle sensor(s) 6 could collect angle information in three axes, and a device capable of determining the position of the probe 4 either in 3D space or relative to the other images could be used to determine the distance of one image from the other images. Such position-determining devices could include a counter connected to the drive motor that propels the probe 4 and simply counts the motor's rotations which correlates to a distance, or an accelerometer connected with the probe 4, or a local GPS or laser tracking device for the probe 4, or an optical movement sensor such as that used in optical mice connected with the probe 4, or any number of other methods to track the movement and/or position of the probe 4. Signals from the angle and position sensors could be simultaneously saved in the same data packet as the image, or collected separately and later correlated with the image. A typical correlation method would be to use a timing mechanism that assigns a time value to both the image and the angle/position information, which could be matched up later, but other suitable correlation methods could be used.

As shown in FIG. 2B, the result of a typical scanning operation is a set of 2D images 16 along with orientation (rotation angle) information 18 and positioning information 20 matched to each 2D image 16. From these elements, the 3D modeling system 21 constructs a solid 3D representation 31 by simply merging all of the 2D images 16 together in 3D space, as shown in FIG. 2C (although depicted as an image on a display in FIG. 2C, the "3D representation 31" is actually a set of data structures in the computer's memory, and only becomes recognizable as an image after the 3D representation has been "rendered" by the computer and subsequently displayed).

As shown in FIG. 1, the software disclosed herein comprises 5 modules: the data source module 22, the frame creation module 24, the texture mapping module 26, the rotation transform module 28, and the translation transform module 30 that, together, convert the individual 2D images 16 and orientation 18 and positioning values 20 into a 3D representation 31 of the source anatomical structure that can be rendered and manipulated on the host computer system 32 (FIG. 2C). Each of the modules is explained in detail below. The number of modules was arbitrarily chosen for discussion purposes and could be combined into fewer or expanded into more without limiting the concepts described herein.

1. Data Source Module

As shown in FIG. 1, the data source module 22 provides a virtualized interface to the scanning and angle sensor portions of the host system. The data source module is responsible for receiving the slice image data 14 from the ultrasound scanning device 10 and, if necessary, converting the image data to a format optimized for texture mapping. In a preferred embodiment, the images may be converted from a proprietary format exported by the scanning device to a standard Windows bitmap format acceptable to the Microsoft Windows Direct3D subsystem for texture maps. The data source module 22 is also responsible for normalizing and transforming the image slices 14 if they must be resized, cropped, or color-corrected before they are suitable for texture mapping. For example, the data source module may convert the images to a grayscale representation of the original. Finally, the data source module 22 is responsible for receiving and normalizing (and in some cases interpolating) the orientation data 18 sent by the angle sensor 6 and assigning rotation angles to the individual slice images, and receiving and normalizing positioning information 20 from the position-determination system. The data source module also converts the unit measurements associated with the position and angle of each image when necessary.

In a preferred embodiment, the data source module 22 receives orientation data 18, positioning data 20, as well as ultrasound 2D image 16 data. By the time these data reach the data source module 22, they may have already been acquired and used elsewhere in a data processing software system to which the invention may be connected as a subordinate module. Thus, in a preferred embodiment it is not necessary for the data source module 22 to concern itself directly with acquisition of the data from the source hardware devices through serial and network connections in the host computer 32 (FIG. 2C)—though it certainly could be expanded to take on these tasks using well-understood and documented prior art techniques. Rather, in a preferred embodiment, the data source module 22 need concern itself only with interfacing with the host software system, acquiring the data from this host software system, converting it into a format appropriate for consumption by the other modules, and dispensing this data to the other modules on request.

The interface to the host software system—like the interface to the other modules—is accomplished by implementing all components as standard C++ objects with well-defined public methods. The data source module 22 extracts data from the host software system by making calls on that host software system's public methods, and the other objects retrieve that data, subsequently, from the data source module 22 by calling public methods on the data source module 22. Internally, to bridge the gap between the host software system and the other modules, the data source module 22 need only convert the angular data extracted from the host software system from angles in degrees to angles in radians, and add a standard Windows bitmap header to each of the 2D images 16.

The hardware-specific details about how images and orientation 18 and position data 20 were actually acquired may be "hidden" from the other modules within the data source module 22. Thus, the 3D modeling system 21 disclosed herein can be made compatible with an imaging system using virtually any type of data acquisition hardware simply by altering this one module. Although the above discussion uses ultrasound images as an example, other types of images could be used, with appropriate minor changes in the manipulation necessary to convert the data into a form that can be used with various computer systems and operating systems.

2. Frame Creation Module

In a preferred embodiment, the frame creation module 24 (FIG. 5) may receive sequential bitmapped 2D images 16, along with their orientation 18 and positioning information 20, from the data source module 22. The frame creation module 24 is responsible for creating the surfaces (planar frames) onto which the bitmapped 2D images 16 will be mapped within the 3D model under construction.

In a preferred embodiment, the range of motion of the probe 4 over the subject tissue is limited to rotations about the x and z axes, and thus a vector parallel to the z-axis may be passed through one upper corner of each of the bitmapped images. As shown in FIG. 4A, this corner becomes the reference point 34 about which each frame is constructed by the frame creation module 24. The reference point 34 could actually be any point on each frame; the same corner point was chosen on each frame in a preferred embodiment just to simplify the calculations and minimize the amount of additional data that must be associated with each 2D image 16. And, again, an embodiment that allows rotational freedom about the x, y, and z axes during image acquisition could be implemented. This may simply require an additional axis angle sensor, as well as minor modifications to the orientation 18 (rotation) and positioning data 20 packet associated with each 2D image 16 to carry the additional information.

FIG. 4A further shows that four coplanar vertices are required for each face of a rectangular planar frame 36. The reference point 34 vertex may be assigned to the origin of the three-dimensional coordinate system in which the model is being constructed. The other three vertices may be positioned relative to the reference point 34 vertex in such a way that the relative dimensions of the planar frame 36 match the relative dimensions of the source image.

In a preferred embodiment, the 3D modeling system 21 may run on a Microsoft Windows personal computer and make use of services provided by the Microsoft Direct3D 3D subsystem (though the 3D modeling system 21 would work as well on other types of computer systems that employ different operating systems and 3D subsystems—for example, on UNIX systems that utilize OpenGL). Direct3D does not provide support for rectangular primitives. So, in a preferred embodiment, the frame creation module 24 may create a rectangular planar frame 36 for each bitmapped image by creating two adjoining triangle primitives 36a, 36b from the set of four vertices.

In order to make the planar frame viewable from "both sides," it typically must be textured on both sides. To facilitate this, two additional triangles may be mapped to four vertices at the same physical positions (in reverse order) to create the "back side" 38 of the planar frame 36. Of course, if there is no need to view the model from the "back side," or if the 3D subsystem being used natively supports viewing texture mapped surfaces from the front or back, only one planar frame, the "front side" 36, needs to be created (and subsequently textured).

The method by which the planar frame creation is accomplished depends on the 3D subsystem being used. In the case of Direct3D, a custom vertex format that incorporates texture mapping coordinates may be created. Typical texture coordinates are within the range [0.0–1.0] from left to right and top to bottom. As shown in FIG. 6, the coordinates may be attached to the four vertices that make up the front planar frame 36 "rectangle." Then, to make the "back" of the planar frame 38 rectangle, the coordinates of the four vertices at the same physical locations may be mapped in "reverse order" as shown in FIG. 6.

This type of planar frame creation in 3D modeling is well within the ordinary skill in the art of 3D computer modeling. Representative modeling techniques are discussed in many references, including Peter Walsh, Adrian Perez, *Advanced 3-D Game Programming using DirectX* 8.0 (Wordware Publishing, Inc. 2001), the disclosure of which is incorporated herein by reference. The above discussion is merely an example of how such planar frame creation could be accomplished, there are myriad other ways of creating such planar frames 36, 38. As noted above, other operating systems and 3D subsystems could be used with equivalent results.

The net result each time a bitmapped image is passed to the frame creation module 24 is the double-sided rectangular planar frame 36, 38 (constructed from four triangle primitives 36a, 36b) depicted in FIGS. 4a and 6.

3. Texture Mapping Module

The texture-mapping module 26 receives sequential bitmapped 2D images 16 along with the planar frames 36, 38 constructed for them by the frame creation module 24. The texture-mapping module 26 is responsible for applying each bitmapped 2D image 16 to its planar frame 36.

Texture mapping is the process by which 2D graphic images are "pasted" onto 3D polygonal surfaces as a "texture." Efficient techniques for texture mapping are well documented in the prior art, such as the above-mentioned Walsh/Perez reference. Typically, texture mapping is used in 3D applications to provide more visual realism to rendered objects—for example, a bitmap image of a stonework pattern can be applied to a surface within a 3D scene to make the surface look like a stone wall. Texture mapping is a complex process involving coordinate mapping and matrix-driven stretch and shear transformations to ensure that a graphic looks correct on the 3D surface to which it has been applied given the shape of that surface and the angle from which it is viewed. Such texture mapping is so commonly used in 3D graphics that practically all commonly sold 3D video accelerator boards for personal computers feature hardware circuitry for directly enabling texture mapping at very high speeds. Typical examples of such video accelerator boards include NVIDIA GeForce4 Ti 4600 and ATI Radeon Rage 128-bit GL, but as noted below, the use of such boards is not necessarily required.

A preferred embodiment of the 3D modeling system 21 may run on Microsoft Windows in the presence of Direct3D services that may directly interface with the texture mapping circuitry on the computer's video accelerator board. When necessary, the highly optimized Direct3D system software can enable texture mapping in the absence of such video accelerator board circuitry. Consequently, the software described herein must do very little texture mapping work. The software of the texture mapping module may simply assign appropriate texture coordinates to each of the vertices that define the front of each planar frame 36 such that each bitmapped image may be mapped to that planar frame 36 from left edge to right edge, from top edge to bottom edge, thus exactly and entirely covering the frame front without cropping, wrapping or leaving any portion of the frame uncovered. Similarly, texture coordinates may be assigned to each of the vertices that define the back of each planar frame 38 such that the mirror image of the same bitmapped image is mapped to completely cover the back of the planar frame 38.

As shown in FIG. 4B, The net result each time a bitmapped (or other suitable format) image is passed to the texture mapping module with a planar frame 36, 38 created in the frame creation module is the double-sided 2D graphic planar frame 40 in 3D space.

4. Rotation Transform Module

The rotation transform module 28 receives sequential double-sided 2D graphic planar frames 40 constructed by the texture-mapping module 26 along with orientation (rotation) information 18 for the graphic planar frames 40. The rotation transform module uses the orientation information 18 to rotate and properly orient each graphic planar frame 40 in 3D space relative to the three component axes.

As described previously, each planar frame 36 may be constructed with its fixed reference point 34 at the origin of the coordinate axes. This reference point 34 may act as the "pivot" about which the graphic planar frame 40 is rotated. Also, as described previously, in a preferred embodiment each planar frame 36 may have only two degrees of freedom and may rotate about the x and z axes, but not about the y axis. Thus, orienting each graphic planar frame 40 in virtual 3D space is a simple matter of constructing an appropriate 4×4 matrix to rotate points about the z axis by the specified z-axis rotation angle ($\theta$ in FIG. 4C) and then multiplying each frame vertex by this matrix, and then constructing a new 4×4 matrix to rotate points about the x axis by the specified x-axis rotation angle (not shown) and multiplying each frame vertex by this matrix. The mathematics involved in constructing such rotation matrices is well-documented in the prior art and should be well known to those of ordinary skill in the art, so it will not be belabored here.

In another embodiment, each planar frame may have three degrees of freedom, and yet the mechanics of the model construction are nearly identical. A common point of reference is chosen at the same location on each planar frame, typically a corner, although any point could be used. This reference point 34 may be used as the pivot for the rotations, and the offset point for all offset position values (implemented in the Translation Transform Module, below). The data source module 22 would then properly associate orientation information 18 (x-rotation, y-rotation, z-rotation), and position information 20 (x-, y-, and z-offset) for each graphic planar frame 40. All other image manipulations would be accomplished as described above. There would be no change to the matrix depths. Although one could use a reference point at a different location on each planar frame, or a different reference point for pivot and offset points, it would add complexity to the program.

The net result each time a graphic planar frame 40 is passed from the texture-mapping module 26 to the rotation transform module 28 is the properly oriented graphic planar frame 40 depicted in FIG. 4C.

5. Translation Transform Module

The translation transform module 30 typically receives sequential, properly oriented 2D graphic planar frames 40 from the rotation transform module 28 along with positioning information 20 for the frames. The translation transform module 30 uses the positioning information 20 to properly offset or translate each graphic planar frame 40 from the reference point 34 in virtual 3D space.

As described previously, in a preferred embodiment each graphic planar frame 40 may be constructed with its pivot corner (reference point 34) at the origin of the coordinate axes; this pivot corner (reference point 34) may remain fixed at the origin after the graphic planar frame 40 passes through the rotation transform module 28. It is relative to this corner, in a preferred embodiment, that position (offset) information 20 is specified. Although a point other than the pivot corner (reference point 34) could be used as both the pivot point and the offset point, the corner is chosen for convenience and to simplify the calculation.

Position (offset) information 20 may be provided to the translation transform module 30 in the form of an [x,y,z] vector. In certain embodiments, the ultrasound image slices 14 may be acquired at a fixed rate, and movement of the probe 4 relative to the contour of the patient's skin surface 12 may be kept constant, and thus the length of each offset vector should remain the same, which simplifies the calculation. In other embodiments, however, each of the components of each vector may vary independently with only a slight increase in calculation complexity. To offset a graphic planar frame 40 to the correct position in 3D space, the translation transform module 30 may construct a 4×4 translation matrix from the specified offset vector. Each of the frame vertices may then be multiplied by the translation matrix. The mathematics and programming involved in constructing translation matrices from offset vectors is well-documented in the prior art and should be well-known to those of ordinary skill in the art, so it will not be belabored here.

Assuming that a series of images is collected in a single row along the x-axis, the x-axis offset will be 0.0 (or some other non-changing value) if the row is straight. If the row is not straight, then x-axis offset information may need to be gathered for each graphic planar frame 40 with respect to a common reference point 34 on each planar frame, and the frame translation module 30 may construct an x-axis offset vector for each graphic planar frame 40. Assuming that images for an expanse of tissue are gathered in two or more rows of images, the frame translation module may take the x-axis offset information for each graphic planar frame 40, and "knit together" a 3D model from these two or more rows. It is not necessary that these rows be substantially parallel, so long as sufficient orientation 18 and position information 20 is obtained for each 2D image 16. To achieve substantially complete coverage for the model, however, the edges of the multiple rows of 2D images 16 should either touch or overlap. The rendering engine, discussed below, should be able to handle any overlap when constructing the model.

The net result each time a graphic planar frame 40 is passed from the rotation transform module to the translation transform module is the properly positioned graphic planar frame 40 depicted in FIG. 4D. Although the z-axis is not shown in FIG. 4D, an appropriate offset vector may be used to translate the graphic planar frame 40 in the z-axis.

6. Rendering the Model

After the model is constructed using the techniques described above, it can be rendered using standard rendering techniques that are handled by the 3D subsystem and/or 3D hardware. These rendering techniques and apparatus are well known in the art and part of virtually every personal computer sold today, so there is no need to describe them in detail here. A reference that generally describes typical rendering techniques is James D. Foley et al., *Computer Graphics: Principles and Practice* (Addison-Wesley Pub. Co. 2nd ed. 1995), the disclosure of which is incorporated herein by reference, but there are numerous other references. Although a preferred embodiment of the 3D modeling system 21 is designed to run on a personal computer, virtually any type of data processing device with sufficient capacity and rendering software/hardware could be used.

The 3D modeling system disclosed herein addresses the practical shortcomings of prior art techniques for constructing solid 3D representations from sets of 2D image slices by using features built into readily available 3D accelerator cards. Nearly all current 3D accelerator cards built into personal computers and workstations feature specialized hardware circuitry for "texture mapping"—a technique whereby 2D bitmapped images can be mapped onto and wrapped around polygonal meshes to add visually realistic texturing to renderings of photo-realistic 3D scenes. Rather than modeling a 3D volume as a set of 3D voxels, the 3D modeling system disclosed herein leverages this high-performance hardware to model the 3D volume as a set of double-sided 2D rectangular frames—each textured with a source 2D image. Strictly speaking, the result of this technique is not identical to mapping pixels to voxels, because each texture element ("texel") remains two dimensional within the 3D model. However, the visualization is generally of very high quality if the source image slices are relatively close together and not parallel to one another relative to all three axes. Also, modeling and rendering performance on personal computers are typically outstanding using this modeling technique.

Another benefit of the 3D modeling system is that where textured rectangular surfaces are used, "back-face culling" (eliminating from the rendering process textured surfaces that do not face the viewer) can be done very quickly during rendering and real-time model rotations (typically, this culling can be done in high-speed dedicated hardware within the accelerator circuitry), making for much better model display performance. In contrast, such circuitry typically cannot perform back-face culling on "points" used in a 3D model constructed with voxels, as the circuitry is typically limited to back-face culling on primitive surface constructs like triangles.

7. Reviewing Methods

One utility of a preferred embodiment is in the area of medical diagnostics. Once a model is constructed using the above techniques, it can be rendered and subsequently viewed and manipulated to identify structures and diagnose medical conditions, such as cancer. For example, images of a breast could be obtained and a model constructed by the above techniques, and subsequently rendered and viewed to screen for or diagnose cancers or other conditions. Any type of cross-sectional series of images could be used, and of any type of tissue or material. Although ultrasound breast tissue images are discussed as an example, the 3D modeling system 21 is not restricted to human tissue or medical diagnostics, and the following methods of review could be used for any 3D model constructed from 2D cross-sectional images.

Ultrasound images may be acquired and converted into a faithful and accurate 3D model of the breast being imaged. The structure of the model facilitates rapid rendering on commonly-available personal computer-based 3D graphics boards. Arbitrary rotations about any combination of axes can be effected with the mouse (or using keyboard controls, or buttons built into the viewer interface) such that the model can be viewed from any angle. The model (and model viewpoint) may be resized so that it may be viewed at larger or smaller sizes on screen. These abilities enable anomalies along the edges of the breast model to be seen easily whereas they might be very difficult to spot if individual ultrasound frames were viewable only one at a time and "head on."

Additionally, the model constructed by the present invention lends itself to a number of manipulations that facilitate the detection of anomalies deep within the modeled tissue. One such manipulation relies on a "clipping plane." The model is first rotated to a desired orientation on-screen. The front view frustrum clipping plane is then advanced (remaining parallel to the screen) through the model, as the model is rendered many times per second. As the clipping plane passes into the model, all portions of the model between the clipping plane and the viewer are removed, enabling a cross-sectional display within the model at a progressively advancing depth. In this way, the inside of the modeled tissue can be viewed from any angle, and at any depth. This enables anomalies or structures that could otherwise escape detection (when viewed from only one particular direction) to be seen clearly. The model may also be rotated when using the clipping plane, to "sculpt" the model.

Still another manipulation relies on transparency. Since the 3D modeling technique disclosed herein relies on 2D texture mapping, alpha channeling can be used to enable transparency and partial transparency (otherwise known as "translucency") of the image frames comprising the model. Basically, during rendering the model textures are manipulated such that certain pixels are made to either display, disappear entirely, or to be partially blended with the pixels "behind" them in the model. Additionally, the colors of blended pixels can be manipulated to enhance the appearance of depth and provide other visual cues. Transparency and translucency allow a model to be viewed from the "outside"—and yet one can still see structures "inside" the model. The viewpoint can even be dynamically moved into a model utilizing partial transparency, and a "fly through" of the model can be effected. The angle of the viewpoint can also be dynamically changed during the "fly through" so the user can "fly to" areas of interest observed during the review. This provides yet another set of "views" of the structure being modeled, and further enhances a physician's ability to detect anomalies that might be difficult to see using standard techniques for viewing ultrasound data.

Importantly, to optimize the utility of views incorporating translucency, a preferred embodiment uses a technique that diverges considerably from the numerous prior art techniques known to applicant. Alpha channeling is implemented in 3D graphics subsystems by expanding the data storage area for each color element one or more bits to associate alpha channel information with the color data. When the color element is rendered by the 3D graphics subsystem, its color can be additively "blended" (to an extent controlled by its alpha value) with the color value already present in the 3D subsystem's depth buffer (due to the previous processing of spatially "deeper" color elements) and the result will ultimately be displayed on screen resulting in the appearance of partial element transparency at that point, as more fully explained below.

In a preferred embodiment, the actual color data for each texel (a texture element, essentially equivalent to a pixel on a texture map image) on each model frame is one of 256 possible grayscale values. Although the following discussion applies to texels, the same techniques can be used on bitmapped images used in environments other than 3D texture mapping, and in such cases pixels are the equivalent of texels. The model is thus created in such a way that an alpha byte (8-bits or 256 different possible values) is associated with each texel on each frame of the model. When translucency is enabled, the user selects a "threshold" value (in the range [0–255] inclusive) via a standard user interface mechanism (i.e., a Windows standard trackbar control, for example), or a preset threshold value may be used. Each texel's alpha value is then computed as follows:

The specific color value for each texel is subtracted from the maximum color value (255) to result in a computed value. The computed value is such that a color value of 255 yields 0, and subsequent decreasing color values are associated with increasing computed values. Each computed value is then compared to the threshold value. If the computed value is greater than (or equal to) the threshold value, the alpha value for that texel is set to 255 (which will cause the texel to be rendered completely opaque by the underlying 3D subsystem). If the computed value is less than the threshold value, it is divided by some user selectable or preset value (such as 8, 16, and 32, which are reasonable divisors that, being powers of 2, also speed processing somewhat). The resulting number becomes the calculated alpha value for the texel. Calculating texel alpha values in this way causes progressively lighter colored texels to be rendered more and more transparently (in a non-linear fashion) until those with particularly light colors beyond some value are not rendered at all (though sometimes a more visually pleasing result is rendered if the alpha values are "floored" at some small value—for example, 1 or 2—just to keep texels from disappearing entirely from the rendering). Implementing translucency in this manner better preserves visual depth cues in the resulting display while removing much of the lighter colored "noise" from the frames and allowing a clean view "into" the rendered model.

To enhance contrast as alpha values are being computed, it is possible to modify one or more of the color components of a texel's color data (if the grayscale data has actually been encoded for each texel as several color components). For example, texels with computed alpha values less than 255 have their green and red color components multiplied by some user selectable or preset value (up to a maximum resulting component value of 255) making progressively more transparent pixels progressively more "yellow." This tends to enhance the apparent contrast of the unmodified, opaque grayscale pixels in the rendering, and also further enhances depth cues. To manipulate contrast or other viewing parameters, such as brightness or gamma, numerous other mathematical manipulations could be made to any color component when the color value of a particular texel falls below the threshold value.

Although a preferred embodiment uses 256 grayscale values, other numbers of grayscales could be used to construct and/or render the model, and the above-described manipulation techniques would work equally well with color data.

What is claimed is:

1. A computer-based 3D modeling system for constructing a virtual 3D representation from a plurality of data images of 2D cross sections having a mutual spatial relationship comprising a data source module through which can be extracted the plurality of data images of 2D cross sections having orientation and positioning information for each of the plurality of data images according to the mutual spatial relationship;

a frame creation module capable of creating a planar frame for each of the plurality of data images from the data source module;

a texture-mapping module capable of mapping each of the plurality of data images from the data source module onto its corresponding planar frame from the frame creation module as a texture;

a rotation transform module capable of using the orientation information for rotating each planar frame from the texture-mapping module about one or more axes in virtual 3D space according to the orientation information;

a translation transform module capable of using the positioning information for translating each planar frame from the texture-mapping module in virtual 3D space according to the positioning information.

2. The computer-based 3D modeling system of claim 1, the translation transform module receiving each planar frame from the texture-mapping module through the rotation transform module.

3. The computer-based 3D modeling system of claim 1, the data source module being capable of converting to a grayscale representation the plurality of data images of 2D cross sections.

4. The computer-based 3D modeling system of claim 1, the data source module being capable of converting the orientation information associated with each data image of 2D cross section to radians from its native angular units.

5. The computer-based 3D modeling system of claim 1, the data source module being capable of converting the positioning information associated with each data image of 2D cross section to fractions of a millimeter from its native measurement units.

6. The computer-based 3D modeling system of claim 1, the frame creation module being capable of creating each planar frame from two adjoining triangle primitives.

7. The computer-based 3D modeling system of claim 1, the planar frames being two-sided planar frames.

8. The computer modeling system of claim 7, the texture-mapping module being capable of mapping each data image of 2D cross section onto each side of the corresponding planar frame as a texture.

9. The computer-based 3D modeling system of claim 8, the texture mapping module being capable of setting the texture associated with each side of each of the planar frames to entirely and exactly fit each side of the frame without cropping, wrapping, or leaving any portion of the frame uncovered.

10. The computer-based 3D modeling system of claim 7, the frame creation module being capable of creating each planar frame from four triangle primitives, two constituting one side of the frame, and two constituting the other side of the frame.

11. The computer-based 3D modeling system of claim 1 further comprising
a data source including an ultrasound scanning device in data communication with the data source module.

12. The computer-based 3D modeling system of claim 11, the data source further including a position determining device and a rotation angle sensor coupled with the ultrasound scanning device.

13. The computer-based 3D modeling system of claim 1, the data source interface converting the plurality of data images of 2D cross sections to a standardized bitmap format.

14. A method for generating a computer-based virtual 3D representation comprising
obtaining a plurality of data images of 2D cross sections along with orientation and positioning information for each data image;
creating a planar frame for each data image;
mapping each data image onto its corresponding planar frame as a texture;
rotating each planar frame about one or more axes in virtual 3D space using the orientation information;
translating each planar frame in virtual 3D space using the positioning infomation displaying the plurality of planar frames on a viewer as a virtual 3D representation.

15. A method of reviewing a computer-based 3D representation generated according to the method of claim 14, comprising
displaying the plurality of rotated and translated frames as a virtual 3D representation on a screen, and reviewing it using one or more of rotating the virtual 3D representation, advancing into the virtual 3D representation using a clipping plane, adjusting the transparency of the virtual 3D representation, adjusting the translucency of the virtual 3D representation, adjusting the color of pixels used to represent the virtual 3D representation on the screen, adjusting the contrast of pixels used to represent the virtual 3D representation on the screen, adjusting the brightness of the virtual 3D representation, adjusting the gamma of the virtual 3D representation, resizing the virtual 3D representation, dynamically translating the viewpoint into the virtual 3D representation, and dynamically moving the viewpoint relative to the virtual 3D representation.

16. A method of reviewing a computer-based 3D representation generated according to the method of claim 14, comprising
displaying the plurality of rotated and translated frames as a virtual 3D representation on a screen and adjusting translucency of the images mapped to the frames by manipulating the alpha value of individual pixels, including obtaining a specific color value for that pixel, selecting a threshold value, calculating a computed value by subtracting a maximum color value from the specific color value, comparing the computed value to the threshold value, setting the alpha value equal to the maximum color value if the computed value is greater than or equal to the threshold value, and calculating the alpha value by dividing the computed value by a selected value if the computed value is less than the threshold value.

17. The method of claim 16 further comprising
adjusting contrast by manipulating the color values of individual pixels, including mathematically modifying at least one color component for pixels with a calculated alpha value less than the maximum color value.

18. A method of reviewing a computer-based 3D representation generated according to the method of claim 14, comprising
displaying the plurality of rotated and translated frames as a virtual 3D representation on a screen, and adjusting translucency of the images mapped to the frames by manipulating the alpha value of individual pixels, including obtaining a specific color value for that pixel, selecting a threshold value, calculating a computed value by subtracting a maximum color value from the specific color value, comparing the computed value to the threshold value, setting the alpha value to the max color value if the computed value is greater than or equal to the threshold value, and calculating the alpha value if less than the threshold value by dividing the computed value by a selected value.

19. The method of claim 18, setting the alpha value to the max color value being if the computed value is greater than the threshold value.

20. A method of reviewing a computer-based 3D representation generated according to the method of claim 14, comprising
displaying the plurality of rotated and translated frames as a virtual 3D representation on a screen, and adjusting translucency of the images mapped to the frames by manipulating the alpha value of individual pixels, including obtaining a specific color value for that pixel, selecting a threshold value, calculating a computed value by subtracting a maximum color value from the specific color value, comparing the computed value to the threshold value, setting the alpha value to the max color value if the computed value is less than or equal to the threshold value, and calculating the alpha value if greater than the threshold value by dividing the computed value by a selected value.

21. A computer-based system for constructing a simulation of a 3D volume comprising
a data source module through which can be extracted a plurality of 2D cross-sectional images and orientation and position information associated with each image;
a frame creation module capable of creating a plurality of planar frames, each image being associated with a corresponding planar frame from among the plurality of planar frames;
a texture-mapping module capable of texture-mapping each image onto the corresponding planar frame;
a rotation transform module capable of rotating each planar frame about one or more axes according to the orientation information associated with the image that is texture-mapped onto each respective planar frame; and a translation transform module capable of translating each planar frame, relative to the one or more axes, according to the position information associated with the image that is texture-mapped onto each respective planar frame.

22. The computer-based system of claim 21, the frame creation module being capable of creating each planar frame from at least two adjoining triangle primitives.

23. The computer-based system of claim 22, the frame creation module being capable of creating each planar frame from four triangle primitives, two of the triangle primitives forming one side of the planar frame, and the other two of the triangle primitives forming the other side of the planar frame.

24. The computer-based system of claim 21, the planar frames being two-sided planar frames.

25. The computer-based system of claim 24, the texture-mapping module being capable of texture-mapping each image onto both sides of the corresponding planar frame.

26. The computer-based system of claim 21, wherein each planar frame has approximately equal relative dimensions as compared to the corresponding image.

27. The computer-based system of claim 21, wherein each planar frame includes a pre-determined point of reference.

28. The computer-based system of claim 21, the translation transform module receiving each planar frame from the texture-mapping module through the rotation transform module.

29. The computer-based system of claim 21, the data source module being capable of converting the images to a grayscale format.

30. The computer-based system of claim 21, the texture-mapping module being capable of texture-mapping each image onto the corresponding planar frame so that the image entirely and exactly fits the planar frame without cropping, wrapping, or leaving any portion of the planar frame uncovered.

31. The computer-based system of claim 21 further comprising a data source including an ultrasound scanning device communicably coupled to the data source module.

32. The computer-based system of claim 31, the data source further including a position determining device and an orientation sensor communicably coupled to the ultrasound scanning device.

33. A method of visually simulating a 3D volume comprising:
obtaining a plurality of 2D cross-sectional images and orientation and position information associated with each image;
creating a plurality of planar frames, each image being associated with a corresponding planar frame from among the plurality of planar frames;
texture-mapping each image onto the corresponding planar frame; rotating each planar frame about one or more axes according to the orientation information associated with the image that is texture-mapped onto each respective planar frame;
translating each planar frame, relative to the one or more axes, according to the position information associated with the image that is texture-mapped onto each respective planar frame; and
displaying the plurality of texture-mapped planar frames on a viewer as a simulated 3D volume.

34. The method of claim 33, wherein creating the plurality of planar frames includes creating each planar frame from at least two adjoining triangle primitives.

35. The method of claim 34, wherein creating each planar frame from at least two triangle primitives includes creating each planar frame from four adjoining triangle primitives, two of the triangle primitives forming one side of the planar frame, and the other two of the triangle primitives forming the other side of the planar frame.

36. The method of claim 33, wherein creating the plurality of planar frames includes creating a plurality of two-sided planar frames.

37. The method of claim 36, wherein texture-mapping each image onto the corresponding planar frame includes texture-mapping each image onto both sides of the corresponding planar frame.

38. The method of claim 33, wherein creating the plurality of planar frames includes creating each planar frame to have approximately equal relative dimensions as compared to the corresponding image.

39. The method of claim 33, wherein creating the plurality of planar frames includes creating each planar frame to include a pre-determined point of reference.

40. The method of claim 33, wherein texture-mapping each image onto the corresponding planar frame includes texture-mapping each image onto the corresponding planar frame so that each image entirely and exactly fits the corresponding planar frame without cropping, wrapping, or leaving any portion of the planar frame uncovered.

41. The method of claim 33 further comprising generating the plurality of 2D cross-sectional images with a data source which includes an ultrasound scanning device.

42. The method of claim 41, wherein generating the plurality of 2D cross-sectional images with a data source includes determining the position and orientation information associated with each image.

43. The method of claim 33, wherein displaying the plurality of planar frames on a viewer includes reviewing the simulated 3D volume using one or more of: rotating the simulated 3D volume; advancing into the simulated 3D volume using a clipping plane; adjusting the transparency of the simulated 3D volume; adjusting the translucency of the simulated 3D volume; adjusting the color of pixels used to represent the simulated 3D volume on the screen; adjusting the contrast of pixels used to represent the simulated 3D volume on the screen; adjusting the brightness of the simulated 3D volume; adjusting the gamma of the simulated 3D volume; resizing the simulated 3D volume; dynamically translating the viewpoint into the simulated 3D volume; and dynamically moving the viewpoint relative to the simulated 3D volume.

* * * * *